(12) United States Patent
Shanbrom

(10) Patent No.: US 6,548,076 B2
(45) Date of Patent: *Apr. 15, 2003

(54) ANTIMICROBIAL LEES

(75) Inventor: Edward Shanbrom, Santa Ana, CA (US)

(73) Assignee: Shanbrom Technologies, LLC, Ojai, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/375,630

(22) Filed: Aug. 17, 1999

(65) Prior Publication Data

US 2002/0102287 A1 Aug. 1, 2002

(51) Int. Cl.[7] ............................................. A01N 25/10
(52) U.S. Cl. ........................ 424/405; 424/409; 424/419; 424/766
(58) Field of Search ............................... 424/405, 409, 424/410, 417–420, 439, 766, 94.2, 94.61, 442, 474, 477; 435/175, 179, 187, 207; 426/2, 52, 53

(56) References Cited

U.S. PATENT DOCUMENTS

| | | | | |
|---|---|---|---|---|
| 2,159,953 A | * | 5/1939 | Proetto | |
| 3,725,341 A | * | 4/1973 | Queuille et al. | 424/80 |
| 3,852,490 A | * | 12/1974 | John | 426/271 |
| 4,851,392 A | * | 7/1989 | Shaw et al. | 514/53 |

OTHER PUBLICATIONS

Americ et al Technology of Wine Making pp 542–545, 643–649, 1980.*

* cited by examiner

Primary Examiner—Neil S. Levy
(74) Attorney, Agent, or Firm—Reed Smith Crosby Heafey

(57) ABSTRACT

The lees or "dregs" produced during wine making are rich sources of antioxidants. Unexpectedly, these materials show significant antibacterial properties as well as antioxidant properties. The lees of red wine which consist of tannins and plant pigments precipitated around crystals of potassium tartarate can advantageously be used directly as a tonic or demulcent. The material can also be used topically for disinfecting the skin, etc. In addition, it is possible to use organic polymers to bind the pigments and/or solubilize them from the tartaric salt to facilitate their use or to make a relatively pure pigment/tannin component.

5 Claims, 1 Drawing Sheet

ANTIMICROBIAL LEES

BACKGROUND OF THE INVENTION

1. Field of the Invention

The present application concerns natural products and more especially valuable materials that can be derived from the byproducts of vinification.

2. Description of Related Art

Currently there is a growing concern on the part of the public that our modern diet of highly processed and refined foods is "missing some essential components" necessary for health and well-being. This "natural food" movement probably derives from at least two sources. First is the discovery of vitamins over the last three quarter's of a century, and the public realization that consumption of apparently adequate food can actually result in a serious deficiency syndrome. It is not hard to imagine that the already discovered vitamins, which are now added back to our refined foods, are but the tip of the iceberg. That is, many other vitamin-like substances may remain to be discovered meaning that our food is presently dangerously deficient in essential nutrients.

Second is the realization that consumption of certain foods—in particular animal fats—seems to result in significant heart and vascular disease. Not only has the public come to learn that apparently complete foods are lacking a key ingredient, but the public has also learned that apparently innocuous and much favored foods are actually silent killers. The question in the public mind is "why did fatty foods suddenly become so deadly?" One answer is that fatty foods have always been harmful but that people didn't used to consume so much of them. Another answer is that lack of physical activity exacerbates the damage caused by fatty food—the American public certainly appears to have grown more sedentary as compared to Americans a century ago. However, the picture is convoluted by certain groups of people that appear to be immune to the dangers of fatty diets.

For example, some Europeans, particularly of Mediterranean origin, appear to consume diets high in fatty foods with little or no medical consequences. Some experts believe this appearance is actually an artifact of relative recent dietary changes that have not yet "caught up" with Europeans. Under this scenario incidence of heart disease should soon increase sharply in those European areas. Other experts believe that "good fat" (e.g., monounsaturated olive oil) neutralizes the other fat in the European diet. This has sparked an olive oil fad in the United States. While the result is undoubtedly widespread culinary improvement, there is as yet no evidence of positive medical consequences. Finally, there is the "red wine connection": many Europeans consume a considerable quantity of red wine, and some experts have opined that a constituent in red wine acts to neutralize the deleterious effects of a fatty diet.

Although some believe that the alcohol in wine is the source of its apparently beneficial properties, it does appear that red wine is more beneficial than white wine. Since both drinks have about the same level of alcohol, one naturally comes to suspect that the coloring component of the wine is the source of the beneficial properties. It is known that the polyphenolic pigments and tannins present in red wine (but largely missing from white wine) are powerful antioxidants. There is already something of an "antioxidant fad" going on in the field of dietary supplements where many people are consuming vitamin A, vitamin C, vitamin E, and various plant polyphenols in hopes of reducing oxidative damage and the presumed aging effects thereof. Thus, the antioxidant properties of red wine falls right into place with this trend although it has not been proven that antioxidant per se are the source of the beneficial properties of red wine.

Therefore, there is a considerable need for providing the apparent benefits of red wine without increasing the public's consumption of alcohol and at a fairly modest expense.

SUMMARY OF THE INVENTION

The present invention involves the discovery that the lees or "dregs" produced during wine making are rich sources of antioxidants. Unexpectedly these materials also show significant antibacterial properties as well as antioxidant properties. The lees of red wine which consist of tannins and plant pigments precipitated around crystals of potassium tartarate can advantageously be used directly as a tonic or demulcent. The material can also be used topically. In addition, it is possible to use organic polymers to bind the pigments and/or solubilize them from the tartaric salt to facilitate their use or to make a relatively pure pigment/tannin component.

DETAILED DESCRIPTION OF THE PREFERRED EMBODIMENTS

Figure 1:
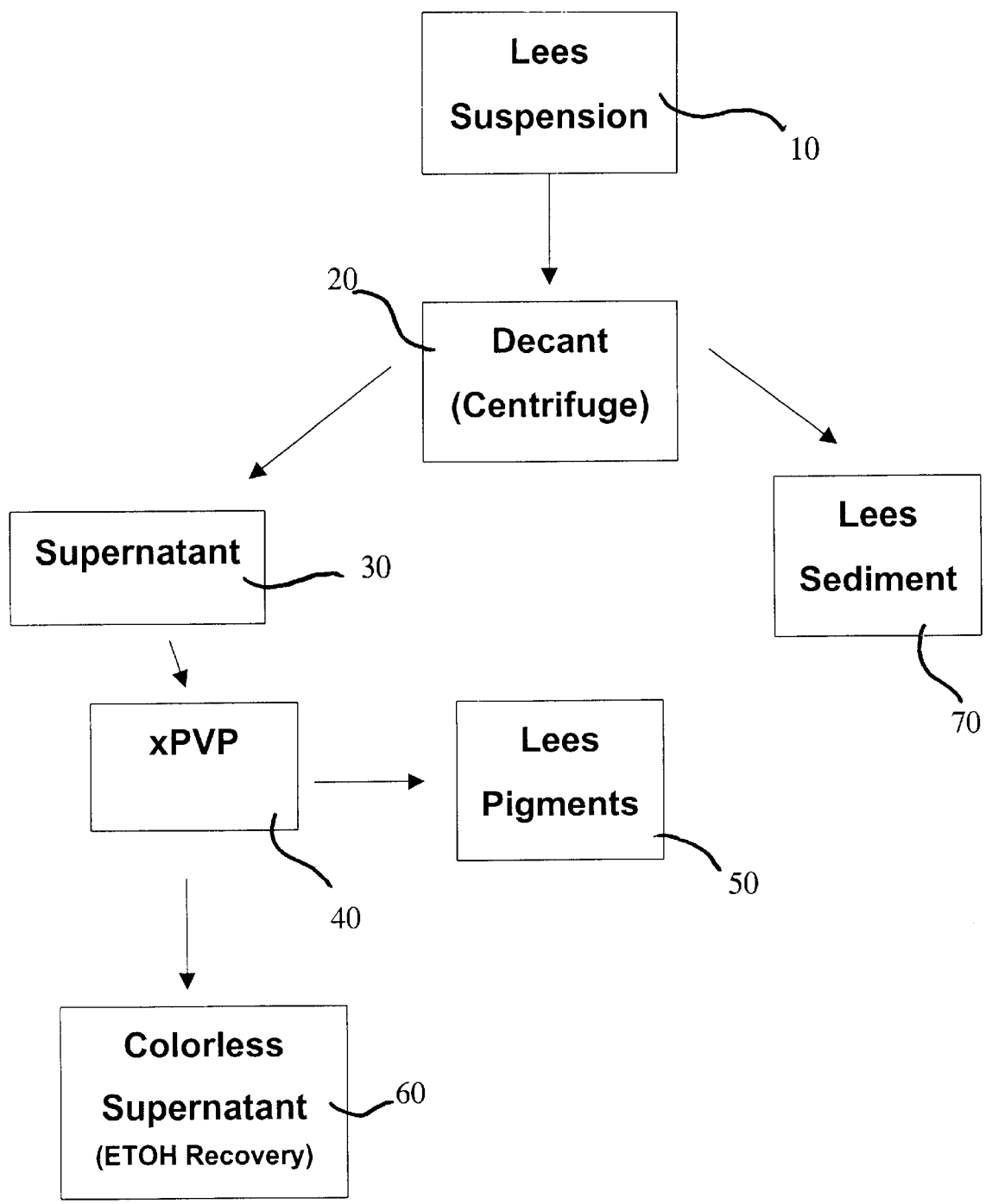
FIG. 1 shows a flow diagram of lees separation.

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide useful compositions from wine lees.

It is not known how the beverage known as wine was first discovered. Suffice it to say that wine goes far back in human history being known from all the classical civilizations that surround the Mediterranean. However, it is clear that wine and wine making go back far beyond those classical civilizations. It is likely that wine making and viticulture (growing of grapes) reaches back well into the New Stone Age and possibly into the Old Stone Age. Many people think that wine is merely fermented grape juice. This description might fit white wine but is certainly incorrect for red wine, the primary beverage of antiquity. This is so because the pigments and tannins that give red wine its color and characteristic flavor are not present in grape juice. The grape skins must be fermented with the juice until the mixture contains sufficient alcohol to liberate the color from the skins. Only then can the skins be pressed to wring out the nascent vintage after which the skins and seeds can be discarded as pommace.

It is not recorded what fortunate person first discovered the transfer of color from skins to wine, but this discovery was essential for the production of wine as a safe and stable beverage. Not only do the pigments and tannins give flavor and color to the wine, they protect the beverage from oxidation and spoilage. It is not likely that wines in the ancient world were normally stored for more than one year. As soon as the fermentation was complete, the wines were sealed in jars and shipped for immediate consumption. Little wonder that wine was generally cut with water or sweetened with sugar of lead as those wines were undoubtedly harsh and tannic.

Later in history, probably in the Middle Ages, it was discovered that under proper conditions wines could be stored for many years and actually improve in sensory quality and drinkability. It was then, when wines were stored, that lees, dregs or sediments first came to be noticed. As wine ages, a slow chemical change occurs. Part of this is due to controlled oxidation as tiny amounts of air seep into the wine. In any case, the pigments and tannins polymerize and tend to fall out of solution. Organic fruit acids such as tartaric acid also precipitate from solution particularly at lower temperatures. This accounts for the dark sediment or lees found in wine barrels and to a lesser extent in wine bottles. This material is removed by filtration or decanting since it renders the wine cloudy and is unpleasant to swallow if present in large quantities.

From time to time some practical use has been made of the lees. They are the primary source of potassium tartarate (cream of tartar), and at one time the lees were extracted to yield a purple pigment used to mark meats and other foods. Nevertheless, the vast majority of lees are simply discarded or returned to the vineyard as a sort of soil amendment. Now I have discovered a number of uses for these materials based on their antioxidant and hitherto unrecognized antimicrobial properties. I have also devised a method for handling the lees to simplify their use.

Lees are obtained from the winery as a suspension of solid material in a quantity of wine. As explained above, the solid material is largely potassium tartarate coated with polymerized tannins and pigments. The first step of my process is to separate the liquid wine from the solid lees. Initial stages of this separation are achieved by gravity decanting and/or by centrifugation. Simple filtration is generally not effective because the almost colloidal lees tend to plug the filter. Once the sediment is largely concentrated, crosslinked polyvinylpyrrolidone (xPVP) is added to the supernatant. This material captures the colors and tannins so that the pigment concentrate can be used as explained later. After the xPVP is removed by filtration or centrifugation, the essentially colorless supernatant can then be flash distilled to recover the ethanol as a byproduct. An outline of this process is shown in FIG. 1. A suspension of lees in wine 10 is obtained from the winery. In a separation step 20 a sediment component 70 is separated from a supernatant component 30 preferably by gravitational means such as decanting or centrifugation. Crosslinked polyvinylpyrrolidone 40 (xPVP) is mixed into the supernatant to capture essentially all of the pigment/tannins 50 which are separated gravitationally. A colorless supernatant 60 that results consists largely of water, alcohol and carbohydrates. The supernatant 60 can advantageously be distilled or otherwise treated to recover the ethyl alcohol. The sediment 70 can be used directly or, as detailed below, can be further fractionated, as with soluble PVP, to liberate the pigments/tannins which can be combined with the pigment/tannins 50 purified from the supernatant 30. Other solid materials can be used to bind the pigment/tannins and can thus be substituted for xPVP. One such material that has worked well in the processes of the present invention is cholestyramine.

Additional Purification

Most attempts to dissolve the purified lees were unsuccessful. Solvents can be used to extract some of the bound pigment but were generally not very effective. For example, sedimented lees 70 were suspended in 5% dextrose, 20% ethanol (ETOH), distilled water, 1.0 M sodium chloride or 0.9% sodium chloride (physiological saline). Some color was dissolved by the distilled water, but the salt solutions were essentially ineffective. Dextrose and ethanol were moderately effective at removing color from the lees.

There are at least two simple effective ways to extract the pigments/tannins from the lees (mostly tartarate crystals). If a suspension of lees are carefully brought to an alkaline pH by drop wise addition of sodium hydroxide, the solid material (tartarate) goes into solution. After this xPVP can be added to precipitate the pigments. The other approach is to add soluble PVP to a suspension of the lees in water. With continued mixing the PVP will bring the pigments/tannins into solution after which the largely colorless tartarate can be removed by centrifugation. The pigments/tannins can be extracted from the soluble PVP if a PVP-free product is desired (e.g., with butanol) or xPVP can be used to render the pigmented components insoluble.

Antioxidant Measurements

Earlier I developed an iodine-based method for measuring antioxidant levels. This method forms the subject of copending application Ser. No. 09/315,688, filed May 29, 1999 and entitled "Method for Quantifying Antioxidant Levels In Foods and Medical Specimens" which is incorporated herein by reference. Briefly, an aliquot of PVP-iodine is added to each sample and reduction of the iodine to iodide was followed with an iodide electrode. Antioxidant units represent the normalized quantity of reduced iodine and are called Iodine Reducing Units (IRU). The measurements were made by taking 4 g aliquots of lees 70 and suspending the aliquots in 25 ml of water to which the iodine reagent is added. The "straight" lees were modified with additives to determine additive effect on the antioxidant determination. The treatments were as follows: a) "straight" lees; b) addition of an equivalent weight of xPVP prior to suspension and addition of iodine; c) addition of 25% soluble PVP (e.g. 1 g; and d) addition of 50% soluble PVP (e.g. 2 g). The results are shown in Table 1.

TABLE 1

| Treatment | IRU |
|---|---|
| a) | 972 |
| b) | 725 |
| c) | 825 |
| d) | 1120 |

Apparently the added xPVP effectively captures some of the pigment/tannin material and prevents it from reacting with the iodine. On the other hand, the addition of soluble PVP, particularly at the higher concentration, appears to liberate the antioxidant material and facilitate its reaction with the iodine.

Additional antioxidant measurements were made of 1 g aliquots of additional grape-derived materials as follows: a) xPVP extract from concord grape juice; b) 50% soluble PVP pigment solution extracted from the material of a); c) lees sediments from merlot wine; and d) lees sediments from concord grape wine. The results are show in Table 2.

TABLE 2

| Treatment | IRU |
|---|---|
| a) | 384 |
| b) | 672 |
| c) | 977 |
| d) | 1590 |

From these results we can see that the wine lees have very high antioxidant levels as compared to materials extracted from grape juice. Again, higher readings are obtained in the presence of soluble PVP. It appears that concord grape wine lees have a somewhat higher level of antioxidants than do vinifera grape (European grape) lees.

Antibacterial Properties of Lees

I have previously discovered that pigment materials extracted from certain fruit juices such as cranberry juice have unexpected antibacterial properties. However, those studies also showed that many fruit juices, such as grape juice, were essentially devoid of antibacterial properties. Therefore, I was surprised to discover that wine lees have significant antibacterial properties. Apparently there is some transformation during the vinification process that augments antibacterial properties. Alternatively, the yeasts contribute antibacterial substances or the entire process concentrates a grape antibacterial substance. Another consideration is that most fruit juices are heated (pasteurized) during processing. It is possible that the antibacterial substances are heat labile. It is my understanding that must for wine production is rarely pasteurized. The antibacterial tests were performed on suspensions ($1 \times 10^3$ bacterial/ml) of *Escherichia coli, Pseudomonas aeruginosa, Staphylococcus aureus*, or *Bacillus subtilis*. One gram of each substance to be tested was suspended in an equal weight of water to produce a 1:2 dilution. Then successive two-fold dilutions were made (1:4, 1:8, 1:16, 1:32, 1:64, 1:128, etc.). One ml of each dilution was added to an equivalent volume of bacteria suspension and incubated at room temperature for 30 min. After this the solution was streaked on nutrient agar and incubated under conditions favorable for bacterial growth. The titer of a material represents the highest dilution that completely inhibited bacterial growth.

The following materials were tested: a) fresh (wet) merlot lees sediment 70; b) dried merlot lees sediment 70; c) lees sediment 70 mixed with 25% (by weight) xPVP; and d) lees sediment 70 mixed with 25% (by weight) soluble PVP. The results for each bacterial species are presented in Table 3.

TABLE 3

|    | E. coli | P. aeruginosa | S. aureusi | S. epidermitis | B. subtilis |
|----|---------|---------------|------------|----------------|-------------|
| a) | 1:128   | 1:128         | 1:128      | 1:128          | 1:64        |
| b) | 1:32    | 1:16          | 1:32       | 1:32           | 1:16        |
| c) | 1:32    | 1:16          | 1:32       | 1:32           | 1:16        |
| d) | 1:64    | 1:16          | 1:32       | 1:64           | 1:32        |

These results show that the lees sediment contains a powerful antimicrobial agent. It appears that solubility of this agent has a significant effect on the overall results. Once the lees have dried the agent is significant less soluble. It is possible that drying destroys the agent, but in most cases activity is partly restored by 25% soluble PVP. This is similar to the results with the antioxidant measurements where soluble PVP increased the availability of the antioxidant material. It appears that the PVP stabilizes and increases the solubility of the antibacterial property of the lees. It is believed that a higher concentration of soluble PVP would completely restore the antibacterial properties of the dried lees sediment.

Significantly, antibacterial measurements made on the concord grape juice "warm tank bottoms" showed very high antioxidant levels showed little antibacterial properties. The "tank bottoms" showed an antioxidant value of 2360 ITU when measured as explained above. In spite of this extremely high antioxidant value the antimicrobial titer against *E. coli* was only 1:4. On the other hand, lees sediment from concord grape wine showed considerable antibacterial properties. Again, some aspect of the vinification process appears to contribute to antimicrobial properties but not to antioxidant properties, or perhaps heating destroys the antibacterial properties.

Antioxidant Tonic/Demulcent

The sediment fraction (tartarate plus pigments) can be processed further to purify the pigments or may be used directly. I have found that this material can be ingested directly as a tonic or demulcent. There is a long history of using potassium tartarate in this fashion. The addition of the polymerized tannins and pigments enhance this effect. This is probably because of the antimicrobial properties of these substances (below). Also, these antioxidant materials are readily absorbed after ingestion as can be monitored as an increase in the antioxidant properties of excreted urine. For example, I ingested approximately 10 g of lees sediment 70 taking samples of my urine both before and after ingestion. Ten ml. samples of urine were tested for antioxidant content using an iodine-based method explained above. By this method it was determined that urine prior to ingestion of the lees had a reading of 278 IRU. After two hours the urine showed 667 IRU; after three additional hours the value had decreased to 518 IRU. This demonstrates that an antioxidant component is readily absorbed from the lees and excreted in the urine. Therefore, there is a significant amount of this material circulating in the blood prior to excretion. With the recent discovery that atherosclerosis may be due to chronic circulating bacterial infections, it is tempting to speculate that the beneficial effects of red wine are at least partially due to the antibacterial substance whose discovery is described above.

Antibacterial Gloves

In checking these materials for antimicrobial properties, I came upon an unexpected use for them. I wished to determine whether these materials have any effect on the bacterial flora of the human hand. I "powdered" a latex glove with finely powdered lees prepared as described. Both hands were sampled for skin bacteria (swab plated on nutrient agar); then a normal powdered latex glove was placed on one hand while a lees powdered glove was placed on the other. After 60 min of wear, the gloves were removed and a second bacteriological sample was taken. As shown in Table 4, the lees completely prevented bacterial growth. The number of plus signs ("+") indicates the amount of bacterial growth.

TABLE 4

|                  | Latex Control Glove | Lees Treated Glove |
|------------------|---------------------|--------------------|
| Start            | +++                 | +++                |
| After 60 minutes | +++                 | No Growth          |

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. Polyvinylpyrrolidofle with anti-bacterial properties produced from lees formed during the vinification of grape juice by first separating solid wine lees from a supernatant fraction, by then contacting the separated solid wine lees with polyvinylpyrollidone, whereby antibacterial properties are transferred to the polyvinylpyrrolidonel, and by next separating the polyvinylpyrollidone with antibacterial properties from the solid separated wine lees.

2. The polyvinylpyrollidone with anti-bacterial properties of claim 1, wherein the separated solid wine lees are contacted with soluble polyvinylpyrrolidone.

3. The polyvinylpyrollidone with antibacterial properties of claim 1, wherein the separated solid wine lees are contacted with crosslinked polyvinylpyrrolidone.

4. Cholestyramine with antibacterial properties produced from lees formed during the vinification of grape juice by first separating solid wine lees from a supernatant fraction, by then contacting the separated solid wine lees with cholestyramine, whereby antibacterial properties are transferred to the cholestyramine, and by next separating the cholestyramine with antibacterial properties from the solid separated wine lees.

5. Water-soluble polyvinylpyrrolidone with antibacterial properties produced from lees formed during the vinification of grape juice by first separating solid wine lees from a supernatant fraction, by then contacting the separated solid wine lees with water-soluble polyvinylpyrrolidone, whereby antibacterial properties are transferred to the water-soluble polyvinylpyrrolidone.

* * * * *